United States Patent
Fine et al.

(10) Patent No.: US 11,754,538 B1
(45) Date of Patent: Sep. 12, 2023

(54) METHOD AND APPARATUS FOR AUTOMATIC CALIBRATION

(71) Applicant: VERO Biotech Inc., Atlanta, GA (US)

(72) Inventors: David H. Fine, Cocoa Beach, FL (US); Edward Bromberg, Orlando, FL (US); Thorsten Schmidt, Cocoa, FL (US); Ryan Denton, Titusville, FL (US); Lucas G. Gamero, Oviedo, FL (US); Gregory Vasquez, Cocoa, FL (US)

(73) Assignee: VERO BIOTECH INC., Atlanta, GA (US)

( * ) Notice: Subject to any disclaimer, the term of this patent is extended or adjusted under 35 U.S.C. 154(b) by 913 days.

(21) Appl. No.: 16/511,928

(22) Filed: Jul. 15, 2019

Related U.S. Application Data

(60) Provisional application No. 62/699,772, filed on Jul. 18, 2018.

(51) Int. Cl.
| | |
|---|---|
| *G01N 33/00* | (2006.01) |
| *G01N 1/38* | (2006.01) |
| *G01N 27/41* | (2006.01) |
| *A61M 16/10* | (2006.01) |
| *A61M 16/12* | (2006.01) |
| *A61M 16/00* | (2006.01) |
| *C01B 21/20* | (2006.01) |
| *C01B 21/24* | (2006.01) |
| *G01N 27/416* | (2006.01) |

(52) U.S. Cl.
CPC ....... *G01N 33/0006* (2013.01); *A61M 16/024* (2017.08); *A61M 16/109* (2014.02); *A61M 16/125* (2014.02); *C01B 21/20* (2013.01); *C01B 21/24* (2013.01); *G01N 1/38* (2013.01); *G01N 27/4162* (2013.01); *G01N 33/0037* (2013.01); *A61M 2202/0275* (2013.01); *A61M 2205/702* (2013.01); *G01N 27/4163* (2013.01); *Y10T 436/100833* (2015.01); *Y10T 436/102499* (2015.01)

(58) Field of Classification Search
CPC ................. G01N 33/0006; G01N 1/38; G01N 27/4162; G01N 33/0037
USPC ........................................................ 436/118
See application file for complete search history.

(56) References Cited

U.S. PATENT DOCUMENTS

| | | | |
|---|---|---|---|
| 5,493,890 A * | 2/1996 | Dussault | G01N 33/0006 73/23.4 |
| 7,914,743 B2 | 3/2011 | Fine et al. | |
| 8,057,742 B2 | 11/2011 | Rounbehler et al. | |
| 2001/0037810 A1* | 11/2001 | Fine | A61K 33/00 128/203.26 |
| 2006/0079740 A1* | 4/2006 | Silver | A61B 5/6882 600/353 |

(Continued)

OTHER PUBLICATIONS

Yang, F. et al, Clinical Chemistry 1997, 43, 657-662.*

(Continued)

*Primary Examiner* — Arlen Soderquist
(74) *Attorney, Agent, or Firm* — Meunier Carlin & Curfman LLC

(57) ABSTRACT

A device and method for calibrating a delivery device includes providing a container A containing a nitrite, providing a container B containing an acid, releasing the contents of containers A and B, allowing the nitrite and acid to mix, waiting for a predetermined time, allowing air to combine with the mixture, and using NO and traces of $NO_2$ to check and calibrate NO and $NO_2$ sensors.

14 Claims, 9 Drawing Sheets

(56) References Cited

U.S. PATENT DOCUMENTS

| | | | |
|---|---|---|---|
| 2006/0180147 A1* | 8/2006 | Rounbehler | C01B 21/24 128/203.12 |
| 2007/0014686 A1* | 1/2007 | Arnold | A61L 2/0094 422/305 |
| 2008/0317874 A1* | 12/2008 | Fine | A61P 9/12 424/718 |
| 2008/0318333 A1* | 12/2008 | Nielsen | G01N 33/0037 436/110 |
| 2009/0314289 A1* | 12/2009 | Fine | A61M 16/16 128/205.27 |
| 2010/0043787 A1* | 2/2010 | Fine | A61M 16/107 128/202.26 |
| 2010/0043789 A1* | 2/2010 | Fine | A61M 16/10 128/203.12 |
| 2010/0089392 A1* | 4/2010 | Fine | A61M 16/12 128/203.29 |
| 2010/0104667 A1* | 4/2010 | Fine | A61K 33/00 128/203.25 |
| 2010/0273272 A1* | 10/2010 | Haas | G01N 33/94 422/86 |
| 2011/0220103 A1* | 9/2011 | Fine | A61M 16/12 128/202.26 |
| 2011/0240019 A1* | 10/2011 | Fine | A61M 16/12 128/202.26 |
| 2014/0127081 A1* | 5/2014 | Fine | A61M 16/12 422/198 |
| 2015/0328256 A1* | 11/2015 | Stenzler | A61K 9/7007 424/718 |
| 2015/0328430 A1* | 11/2015 | Miller | A61K 33/00 128/203.14 |
| 2016/0346498 A1* | 12/2016 | Tector | A61B 5/14551 |
| 2016/0363570 A1* | 12/2016 | Blackley | A61M 15/0003 |
| 2017/0165294 A1* | 6/2017 | Dasse | A61M 16/104 |
| 2018/0071467 A1* | 3/2018 | Fine | A61M 16/10 |

OTHER PUBLICATIONS

Zhang, X. et al, Electroanalysis 2002, 14, 697-703.*
Zhang, X. et al, Frontiers in Bioscience 2004, 9, 3434-3446.*
Toda, K. et al, Analytica Chimica Acta 2007, 603, 60-66.*
Xu, T. et al, Electroanalysis 2014, 26, 449-468.*

* cited by examiner

METHOD AND APPARATUS FOR AUTOMATIC CALIBRATION

CROSS REFERENCE TO RELATED APPLICATIONS

The present application claims priority to U.S. Provisional Pat. App. Ser. No. 62/699,771, entitled "Method and Apparatus for Automatic Calibration," filed Jul. 18, 2018, the disclosure of which is incorporated herein by express reference thereto.

TECHNICAL FIELD

The invention relates to automatic calibration of gases.

BACKGROUND

Nitric oxide (NO), also known as nitrosyl radical, is a free radical that is an important signalling molecule in biological systems. For example, NO can cause smooth muscles in blood vessels to relax, thereby resulting in vasodilation and increased blood flow through the blood vessel. These effects can be limited to small biological regions since NO can be highly reactive with a lifetime of a few seconds and can be quickly metabolized in the body.

Some disorders or physiological conditions can be mediated by inhalation of NO. The use of low concentrations of inhaled NO can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide can also be used to treat chronic pulmonary hypertension, bronchopulmonary dysplasia, chronic pulmonary thromboembolism and idiopathic or primary pulmonary hypertension or chronic hypoxia.

Generally, NO can be inhaled or otherwise delivered to the individual's lungs. Providing a therapeutic dose of NO could treat a patient suffering from a disorder or physiological condition that can be mediated by inhalation of NO or supplement or minimize the need for traditional treatments in such disorders or physiological conditions. Typically, the NO gas can be supplied in a bottled gaseous form, diluted in nitrogen gas ($N_2$). Great care should be taken to prevent the presence of even trace amounts of oxygen ($O_2$) in the tank of NO gas because the NO, in the presence of $O_2$, can be oxidized to nitrogen dioxide ($NO_2$). Unlike NO, $NO_2$ gas can be highly toxic at the part per million level, because if inhaled $NO_2$ can form nitric and nitrous acid in the lungs.

FDA approved devices for delivering inhaled NO typically require calibration before being used on a patient, and then at regular intervals, which could be once a day, or less frequently up to once a month or more, depending upon the circumstances. Sometimes more frequent calibration is appropriate. The calibration consists of checking the detector that senses and reports the concentration of the drug, NO, that is being delivered to the patient, checking the detector that senses and reports the concentration of the drug, NO, that is being delivered to the patient, checking the detector that senses and reports on the nitrogen dioxide ($NO_2$) impurity in the gas being delivered to the patient, checking the oxygen ($O_2$) concentration for those systems that use NO diluted in nitrogen gas. For NO and $NO_2$, both the zero drift and the response to a test gas are typically measured. For $O_2$, typically an air control is all that is needed.

It would be highly desirable to accomplish the calibration automatically from time to time, without user input.

SUMMARY

Some embodiments described herein relate to a method for calibrating a delivery device that can include providing a container A containing a nitrite, providing a container B containing an acid, releasing the contents of containers A and B, allowing the nitrite and acid to mix, waiting for a predetermined time, allowing air to combine with the mixture, using NO and traces of $NO_2$ to calibrate NO and $NO_2$ sensors, and using the air stream to set a zero level.

In other embodiments, a method for calibrating a delivery device includes releasing droplets of a solution A containing a nitrite to a target, releasing droplets of a solution B containing an acid to the same target, allowing the droplets of solution A and solution B to mix and produce NO gas, and controlling the number and frequency of droplets to produce a desired NO concentration.

In certain embodiments, a system for calibrating a delivery device includes container A configured to release a nitrite, container B configured to release an acid, wherein container A and container B are connected to a common air pocket designed to allow the nitrite and acid to mix, an NO sensor, an $NO_2$ sensor, and a controller configured to control the amount of solution A and solution B to a released common target.

In some embodiments, a system for automated calibration can include a calibration module that fits into the place of a cassette, the calibration module containing a reservoir of chemical supplies comprising: chemical reagents for calibration and an ink jet, and a platform that receives the calibration module.

In some embodiments, a system for automated calibration can include a single container with preconnected tanks of compressed NO and $NO_2$, an internal regulator with a pressure gauge, and a flow restrictor that regulates gas flow, a sensor module that detects oxygen, NO and $NO_2$ concentration in a gas flow, and an electronic board containing logic to monitor the pressure gauges on the gas tanks to sure there is sufficient gas to perform calibration, a computer controlling the automatic operation of the flow restrictors.

According to another embodiment, method for real-time calibration without requiring calibration gases can include providing an on-board arrangement of an NO sensor; a $NO_2$ sensor; and an oxygen sensor, together called a calibration module, pumping a gas sample containing unknown concentrations of NO, $NO_2$ into a small balloon, continuously drawing a gas sample from the balloon through the sensor module and measuring the rate of loss of NO and/or the rate of gain of $NO_2$, and calculating the NO and/or the $NO_2$ concentration from the rate of change, and, if the accuracy of the calibration is outside of ±20%, adjusting the sensors to bring them into calibration.

In certain embodiments, the NO can be provided through a cartridge that converts NO-releasing agents to NO. The cartridge can include an inlet, an outlet, and a reducing agent. The cartridge can be configured to utilize the whole surface area in converting NO-releasing agents to NO. The cartridge can have a length, width, and thickness, an outer surface, and an inner surface, and can be substantially cylindrical in shape. The cartridge can have aspect ratio of approximately 2:1, 3:1 or 4:1. The length can be, for example, one inch, two inches, three inches, four inches or five inches. The width can be, for example, 0.5 inch, 1 inch, 1.5 inches, 2 inches, or 2.5 inches. The cartridge can have a cross-section that is a circle, oval, or ellipse (having two foci). In certain embodiments, opposing sides along the length of the cartridge can be flat, resulting in a cross section having flattened parallel sides and rounded parallel sides, similar to a racetrack configuration. The thickness between the inner and outer surface can be constant, thereby providing a uniform exposure to the reducing agents. The thickness can be approximately 1 mm, 2 mm, 5 mm, 10 mm, 20 mm, 30 mm, or 40 mm for example.

In some examples, the cartridge is configured to utilize the whole surface area of the cartridge in converting NO-releasing agents to NO. In some cases, NO only can be generated. By having a fixed volume and a fixed time, and a known O2 concentration, the amount of $NO_2$ generated from the NO can be calculated from the known kinetic equation and the known rate constant. Under these conditions, both NO and $NO_2$ can be determined If $NO_2$ is evolved, it can be converted to NO using various cartridge technologies described above, including the use of an antioxidant such as ascorbic acid. While some configurations allow for the production of sufficient NO and/or $NO_2$ to reach a pseudo-equilibrium concentration, it may take several minutes, it has been found that pseudo-equilibrium conditions are not required. Instead of allowing pseudo-equilibrium to be reached, the chemicals are mixed such that the amount of NO and/or $NO_2$ that is produced is effectively identical every time and that the NO and $NO_2$ levels that are produced at a known elapsed time are effectively identical. The elapsed time could be 1, 2, 3, 4, 5, 6, or more minutes, depending on the situation. Then the shape of the generation curve and other characteristics of the curve can be used to provide data which correlates with a calibration plot against equilibrium values. Thus, a calibration could be completed in less time than it takes for the concentration of the compounds to reach (pseudo)equilibrium.

A significant advantage of generating the NO and/or $NO_2$ on the fly in real time in air is that the NO and/or $NO_2$ are being presented to the instrument in air, and not, as with gas tanks, in nitrogen for NO and nitrogen or air for $NO_2$. It makes little sense to measure NO in air or oxygen enriched air and calibrate with NO in nitrogen. Yet this is what is normally done today.

Other features, objects, and advantages will be apparent from the description, drawings, and claims.

DETAILED DESCRIPTION

Figure 1:
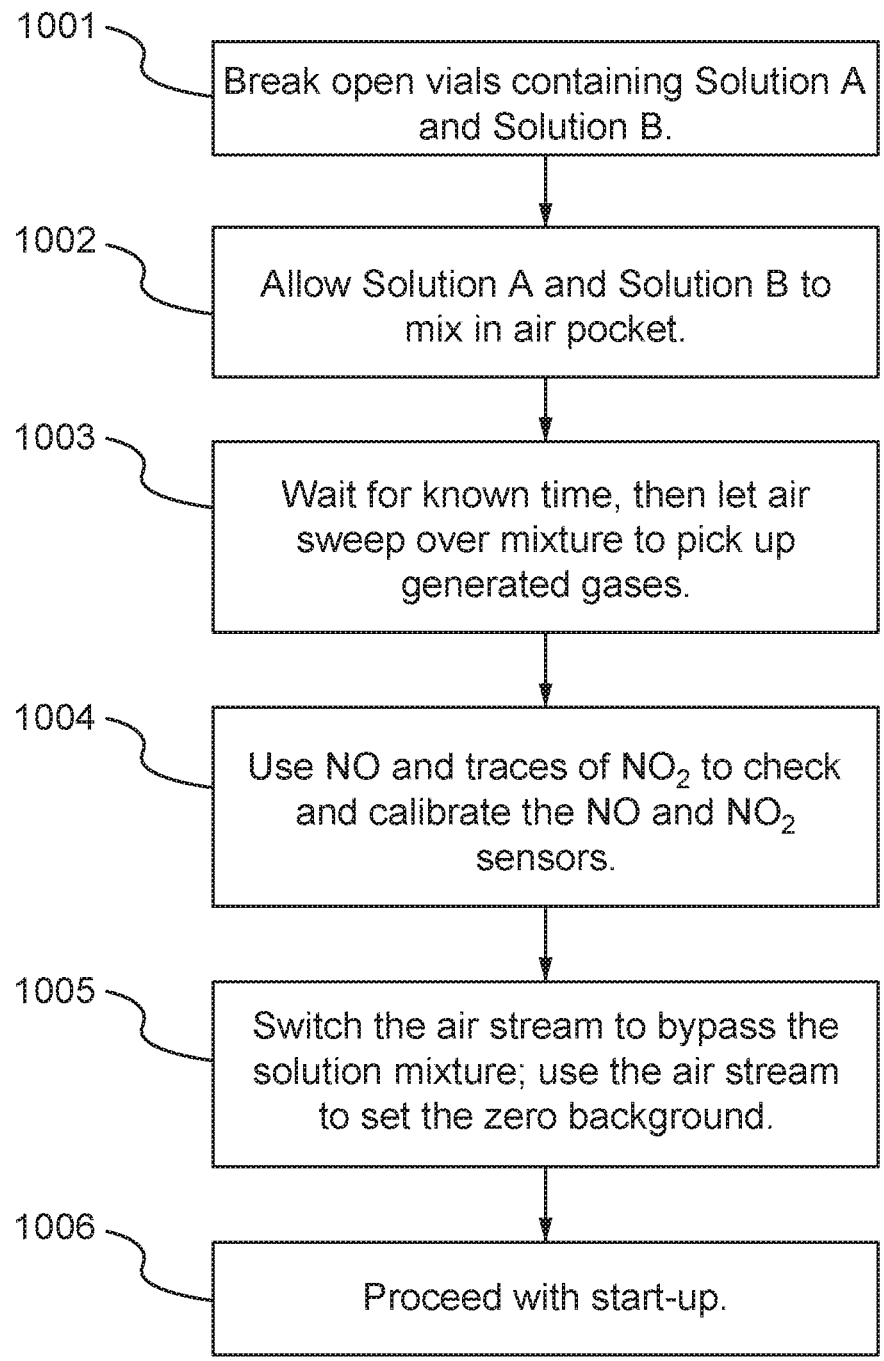
FIG. 1 is a flow chart of a method that mixing two solutions to produce NO and/or $NO_2$, that can be used for automatic calibration purposes, according to an embodiment.

The administration of NO according to the claimed system and methods, allows for a more efficient calibration of delivery systems. Such systems can promote a more pure, controlled and accurate delivery of NO, which achieves enhanced efficiency, safety, and efficacy.

In conventional commercial instruments as used in a hospital for the delivery of inhaled NO, the sensors are typically based on electrochemistry. Such devices typically have a linear response, so that if one calibrates the device at zero and a concentration close to full scale, one determines a calibration curve over the complete range. Examples of commercial suppliers of these sensors include Citicells and Alphasense.

Conventional calibration procedures require the use of specially made and certified calibration gases. One supplier of these calibration gases is Airliquide, which provides small disposable aluminum cylinders. The calibration procedure involves taking the calibration gas cylinders to the NO delivery device and switching the instrument to the calibration mode. A small gas flow from the cylinder that contains the calibration gas, is allowed to flow past the sensors and the instrument response is compared with the previous calibration. If any drift has occurred, the calibration settings are reset. Typically, the calibration is not reset if the drift is small, of the order of 5 to 10%, depending upon the requirements. Similarly, the zero control is set by sampling ambient air and checking that the zero level has not changed with time. Since treatments with concentrations at 1 PPM or below may sometimes be required, in order to increase the accuracy of the device under these use conditions, instead of directly using ambient air to set the zero, the ambient air is first passed through a scrubber to remove substantially all NO and $NO_2$ contaminants prior to performing the zero calibration. During calibration the NO delivery devices are typically not sensing the concentration of NO and $NO_2$ gas that is being delivered to the patient. This makes for a tedious and complex process that typically has to be carried out for every patient. The electrochemical sensor for NO operates based on a bias voltage, even when they are being shipped and stored or are not in use. If the battery that supplies the bias voltage fails, the sensor does not perform properly. For this reason, calibration is typically performed before each patient. Calibration using small tanks of pressurized calibration gas is a sensitive procedure that should not be performed by personnel without special training and experience with the equipment. In particular, care should be taken to properly close the gas valves after use or the gas could escape. In addition, care should be taken to minimize back streaming of air into the calibration gas cylinder, which will cause reduction in the NO by oxidation with O2 to form $NO_2$, or the reaction of $NO_2$ in an $NO_2$ cylinder with humidity in the air to form nitric acid. Nurses and ventilatory therapists in an Intensive Care Unit, where such equipment is typical used, do not normally work with metal cylinders that contain compressed gas, and therefore may not be experienced with the calibration of such delivery devices.

One approach for calibrating delivery devices is to have the calibration gases permanently plumbed into the delivery system. Using computer controlled gas valves, and preprogramed timing and sequencing, the calibration can be carried out automatically. Such a computer-controlled system, however, introduces significant additional complexity and cost. Furthermore the physical space needed to have two more gas cylinders permanently attached to the delivery device. Significantly increases the physical space occupied by the delivery device.

A far simpler and improved method is described herein that involves the synthesis of NO (and/or $NO_2$) used for calibrating the delivery device from suitable chemicals and then passing the NO and/or $NO_2$ gas past the gas sensors. Some embodiments described herein involve the use of Zwitterions, decomposition of N-nitroso compounds, decomposition of nitro organics, and oxidation of Nitrogen contain molecules to produce NO. Those skilled in the art will recognize that additional chemistries for the production of NO and/or $NO_2$ are possible and fall within the scope of the present disclosure.

Some embodiments described herein relate to the mixture of two solutions, one containing a nitrite and the other an acid. The reaction produces NO gas and some $NO_2$ gas, which can then be passed over the sensors. Depending upon the concentration and the residence time, some of the NO produced will also be converted to $NO_2$. Examples of suitable nitrates are sodium or potassium nitrite, the latter compound being widely used to pickle meat. Sodium nitrite is also a food additive for preserving bacon, for example. Examples of suitable acids include acetic acid, ascorbic acid, or even a carbonated beverage. Ascorbic acid has the disadvantage that it may decompose with time, whereas acetic acid (vinegar) is much more stable. In practice, any nitrite salt and any acid can be used.

Thus, some embodiments described herein can use the mixture of a nitrite salt and an acid. The nitrite salt can be dissolved in a suitable solvent (e.g., water) to form a solution (solution A). The nitrite content of a solution A can be accurately measured and/or be US National Institute of Standards and Technology (NIST) traceable. The amount of acid (solution B), is not critical as long as the concentration and volume is sufficient to react with all of the nitrite. The process would be initiated by mixing solutions A and B, waiting for a predetermined time, and then sweeping the gases that are generated across the detectors that are to be calibrated. Reproducibility is dependent upon the concentration and amount of the nitrite solution, ensuring enough acid for reaction. Because the NO and/or $NO_2$ gases are being produced continuously, it can be important to accurately control the time between mixing and exposing the generated gases across the detectors.

Several mechanical aspects can be used in conjunction with methods described herein. The simplest is to provide pockets of Solution A and B, and mechanically break them open, allowing the contents to mix and then waiting a few seconds to minutes for the reaction to occur and then flushing the gas that is generated passed the sensors. Since the NO gas would be generated in an air pocket, the $O_2$ in the air will slowly start to convert the NO to $NO_2$, according to the known reaction kinetics. The gas mixture of NO and traces of $NO_2$ in air would then be used to calibrate the sensors. Since the concentrations of the two solutions are accurately known, and the time of starting the reaction is known, a precise and reproducible amount of NO would be generated in each case each time the procedure is performed using predetermined timing. This physical arrangement is particularly suited to the use of a nitrogen dioxide conversion cassette.

In one embodiment, solutions A and B can be included in a cassette or other suitable calibration device. Referring to FIG. 1, when a new cassette was inserted into the console, the sequence for automatic calibration would be to:

1. Break the two vials that contain solutions A and Solution B (step 1001) and
2. Allow then to mix in an air pocket (step 1002).
3. Wait a known (e.g., predetermined) time and then let air sweep over the mixture to pick up the gases that are generated (step 1003).
4. Use the NO and traces of $NO_2$ to check and calibrate the NO and $NO_2$ sensors (step 1004).
5. Switch the air stream to bypass the solution mixture (step 1005). The air stream can be used set the zero background. Alternatively, Step 1005 can be performed prior to Step 4.
6. Proceed with the start-up of the cassette sequence.

In this manner a calibration traceable to NIST will be performed every time a new cassette was loaded into the console. The console does everything, and there is no input required from the operator.

When two or more chemicals are needed to produce the compound of interest, various procedures for introducing the compounds can be used, including moving belt techniques, adding a solid to a liquid, breaking or bursting a vial including those made from glass or plastic which contain at least one of the reagents and allowing them to mix with the second reagent, and/or having both reagents mix after breaking or bursting a glass or plastic or thin metal containers that contain both.

In other configurations other chemistries can be utilized. Any molecule that can be made to release NO or $NO_2$ can be used. Another configuration that has been used is to wet a material such as filter paper or cotton cloth with a nitrite salt solution and then add drops of the acid to the paper (or vice versa). The paper could be part of a moving belt system.

Other methods and chemistries include the thermal decomposition of certain (typically non-carcinogenic) N-nitroso, S-nitroso, and/or O-nitroso compounds such as diphenyl nitrosamine and N-nitroso-proline. Such nitroso compounds release NO upon thermal decomposition. Thermal decomposition of organic nitro compounds such as nitroglycerin and ethylene glycol dinitrate that release $NO_2$ can also be used. Similarly, organic compounds including ammonia and the hydrazines that contain N-atoms can be burned in a flame or oxidized in an oven at temperatures of greater than about 600° C. A nickel wire wound into a small coil, much like an incandescent filament for a light bulb, has been shown by Fine et al. to work well at breaking nitroorganics into $NO_2$ and then converting the $NO_2$ into NO. Silver wire has also been shown to work well, even at temperatures as low as 200° C. A cigarette, for example, which burns at about 800° C., is hot enough to convert the nitrogen in organics such as nicotine into NO, as well as inorganic nitrates from the tobacco. A small oven can be used or the vapors or gases can pass over a wire coil that has been heated to the appropriate temperature. The amount of the reactants can be small, as the typical calibration range is between 5 to 10 ppm range for NO and less than 1 ppm for $NO_2$.

In other embodiments, zwitterionic polyamine/NO adducts are known to release NO under certain conditions. Another source of NO and $NO_2$ could be small gas tanks with regulators and valves that function under computer control to provide an accurate and known concentration of NO and/or $NO_2$.

Figure 2:
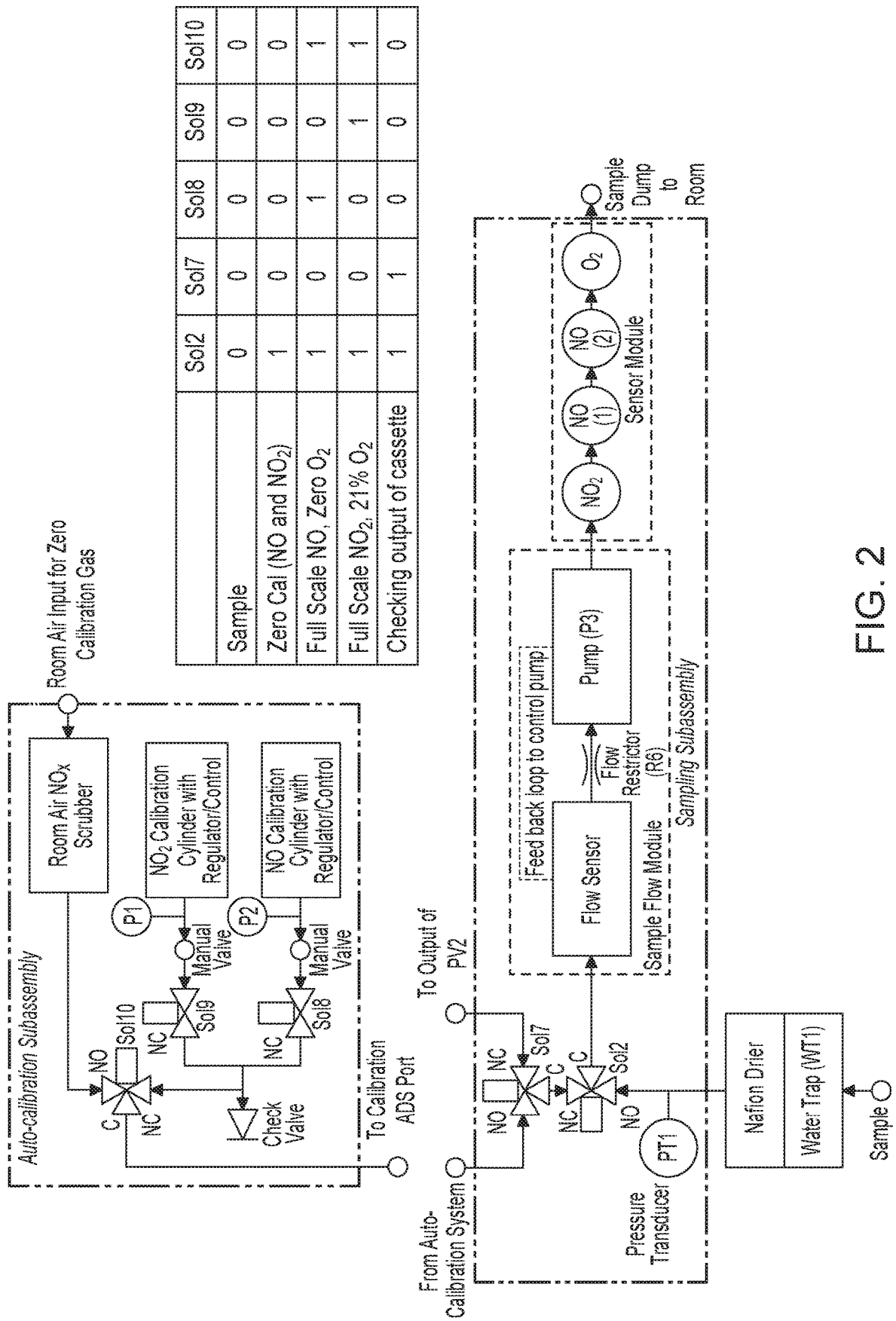
FIG. 2 is a schematic illustration and flow diagram of a system for using automating the use of conventional calibration gas cylinders of NO diluted in nitrogen and $NO_2$ diluted in air, according to an embodiment. The system is shown with a single calibration gas flow path.

Referring to FIG. 2, in certain embodiments, a calibration module, would be self-contained. If the calibration cylinders are small enough, they could be incorporated into an enclosure slightly larger than the size of a cassette. The calibration module or cassette could contain the following components:

Three solenoids inside the calibration module:
Sol8—Opens NO flow.
Sol9—Opens $NO_2$ flow.
Sol10—Chooses between zero air, or full scale gases.

A NO calibration kit including NO cylinder with, for example, 45 PPM NO in nitrogen and integral regulator with pressure gauge, manual on/off valve and flow restrictor to set flow, similar to current NO calibration gas. In contrast to manual calibration techniques, a dial pressure gauge could be replaced with an electronic gauge, and the output flow could be lower.

A $NO_2$ calibration kit can be similar to NO calibration kits described above but can produce, for example, 10 PPM $NO_2$ in air.

A zero scrubber can remove NO or $NO_2$ from the ambient air sample.

A check valve can ensure that the gas sampling system is not starved for sample. The flow from the calibration gas cylinders can be set somewhat above the sampling module requirement, with the excess dumping through the check valve.

An output port for the calibration gases.

A small electronic board can contain the logic to actuate Sol8, Sol9 and Sol10 as required, and to monitor the pressure transducers on the gas cylinders to insure there is adequate gas to perform calibration. This board could also be incorporated into the console electronics.

A USB port can allow for communications between the auto-calibration module and the ADS console to control the switching of the solenoids during the calibration sequence.

One or more of an internal chargeable battery, that is charged via the USB port, a separate power input, or, for example if the power requirements are low enough, the power from the USB while connected to the main ADS console may be adequate to operate the auto-calibration module.

In addition, the automation can activate two solenoids that are already in the Console. The two solenoids in the console are:
Sol2—Chooses between sample and calibration input
Sol7—Chooses between calibration gases or checking during flush if there is any NO output of the cassette.

Figure 3:
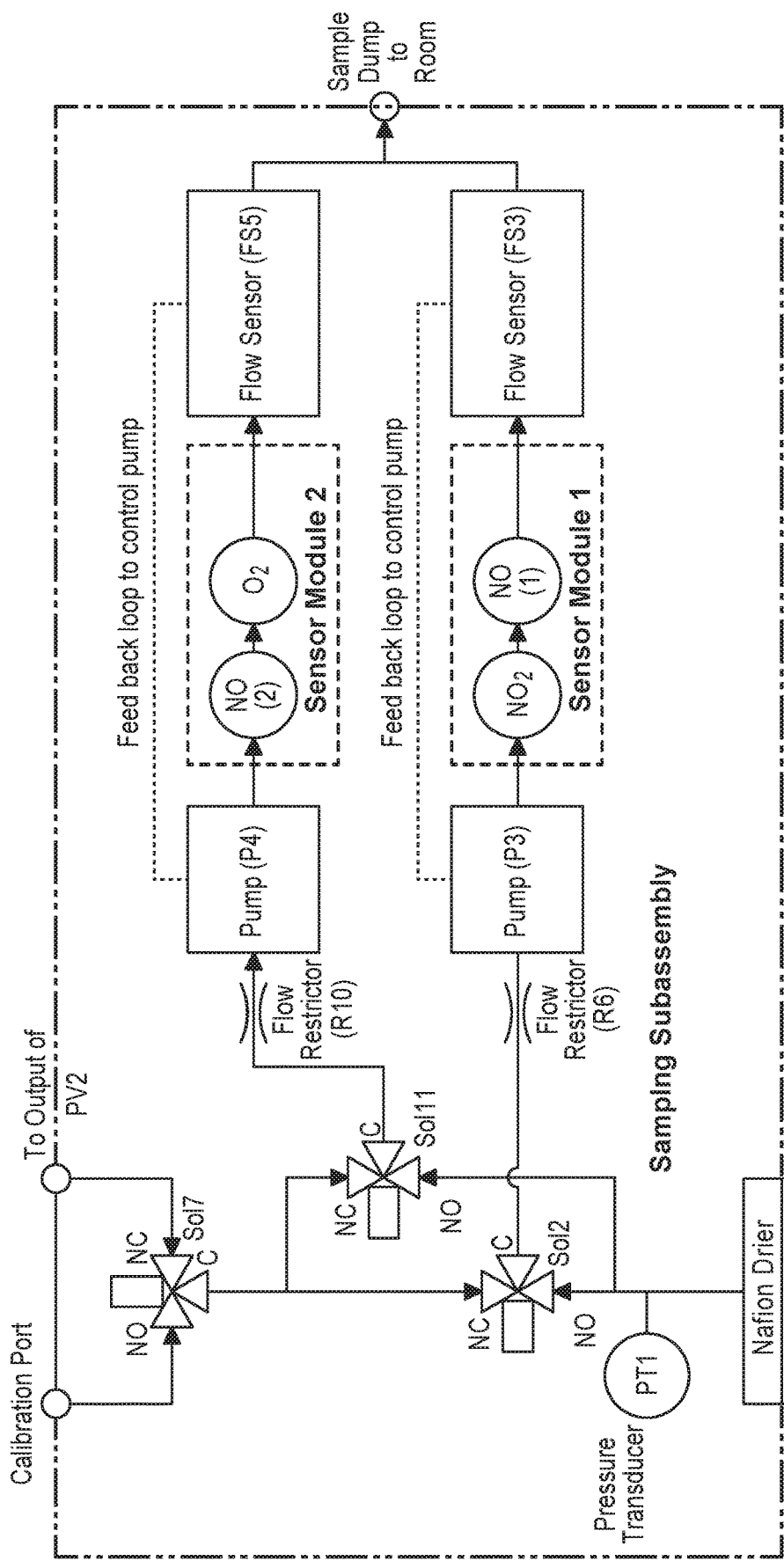
FIG. 3 is a schematic illustration and flow diagram of a system for using automating the use of conventional calibration gas cylinders of NO diluted in nitrogen and $NO_2$ diluted in air, according to an embodiment. The system is shown with two independent gas flow paths for calibration.

Referring to FIG. 3, for a dual flow path sensor module, the auto-calibration would be similar to that of FIG. 2, except that it would also interface with sol11 in the console. In certain embodiments, the calibration procedure can be performed as follows:

Connect the auto-calibration system to the ADS by connecting the USB ports, and the gas output to the calibration port on the ADS.

Open the two manual valves. The two manual valves could be replaced with high quality electronic shut off valves as long as the leak rate is undetectable.

From the GUI of the GeNOsyl Acute DS, command the auto-calibration procedure.

The computer logic would then command the proper solenoids to activate or deactivate to allow for the proper gases to flow into the sample module to perform the different calibrations. FIG. 2 includes a summary table of the states of the solenoids valves to perform the different operations.

The complete process including flushing the system should take about six minutes.

When completed the GUI will issue a message. The operator would close the two manual valves if this function was not automatic.

The calibration system could either be disconnected, or left connected and ready for the next required calibration.

When flowing scrubbed room air, the NO and $NO_2$ sensors are calibrated for the zero point. Since it is sometimes desired to have 1 PPM or lower set points, scrubbed air is used.

The next step would be to flow NO in nitrogen to perform the full scale calibration of the NO sensor, and to simultaneously perform the zero calibration of the oxygen sensor.

Flow $NO_2$ in air containing, typically, 21% oxygen to perform the full scale calibration of the $NO_2$ sensor, and to calibrate the oxygen sensor to the ambient oxygen concentration (e.g., 21%). Typically, scrubbed room air in not used for the ambient oxygen concentration calibration, because it may be preferable to first perform the zero calibration followed by the calibration being challenged with the actual gas being measured.

Calibrating the oxygen sensor at the ambient oxygen concentration for this application is adequate and is much simpler than having to connect to the oxygen that is typically piped into the hospital.

If desired the auto calibration system can be left mounted on the cart and permanently connected to both ADS units on the cart.

Figure 4:
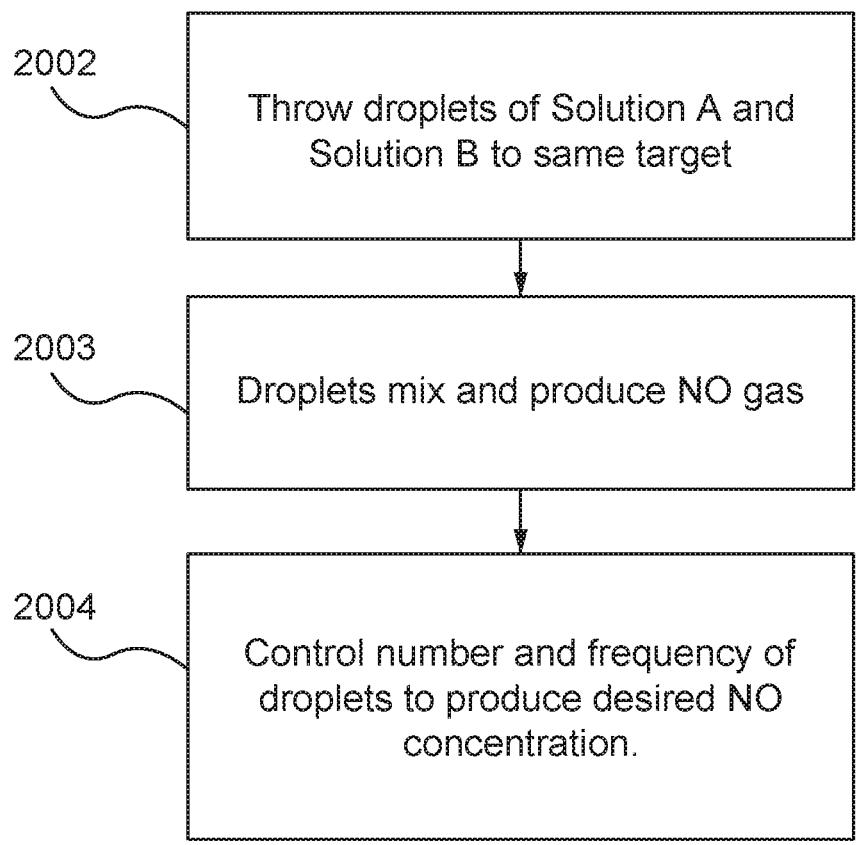
FIG. 4 is a flow chart of a method for using ink jet proportional valves to deliver the chemistries of a two part system, according to an embodiment.

Referring to FIG. 4, another process would be to use two ink jet-style proportional valves to throw tiny droplets of solution A and solution B at the same target (step 2002). The two droplets would mix and react to produce NO gas (step 2003). The number of droplets and their frequency could be controlled to produce any desired NO concentration (step 2004). Also, the droplet stream could be maintained for many seconds to many minutes such that a steady concentration of NO gas could be produced.

As discussed above, the total amount of NO or $NO_2$ produced from suitable chemistries of solution A and solution B can be NIST traceable. The instantaneous amount of NO and/or $NO_2$ at a given time, however, may vary based upon operational conditions such as temperature. Therefore, to increase the accuracy of the calibration, measurement of the NO detected by the electrochemical cell can be integrated over the period of time from when the chemical reaction begins until when the amount of NO or $NO_2$ produced is stable. Since the total quantity of NO or $NO_2$ produced is known and NIST traceable, the integrated NO or $NO_2$ value, along with the calibrated measured gas stream flow, can be compared to the expected value based upon the known amounts of material in the calibration standards, and a calibration correction determined, if needed.

In an exemplary embodiment, the calibration system and methods can be used with a system referred to as the Acute Delivery System (ADS) that uses liquid $N_2O_4$ to generate NO, which is then delivered to the patient. The delivery can be used with a nasal cannula, a face mask, or by means of a ventilator or anaesthesia machine. In this embodiment, the $N_2O_4$ is heated from about 35 to 80° C. to vaporize and dissociate the $N_2O_4$ into $NO_2$ gas. The $NO_2$ gas is then passed through a narrow bore restrictor that controls the amount of $NO_2$ released to the very low therapeutic value, into an air stream that is generated from a small air pump. The air could also come from the hospital air supply. Oxygen could also be used.

In certain embodiments, a dual heater system is configured to keep the temperature of the restrictor at a temperature at least 5° C. above the temperature of the vessel containing the $N_2O_4$ and thereby ensuring that there is no condensation in the restrictor. Depending upon the conditions, the restrictor temperature can be at least 8° C., or 12° C. or 16° C. or 20° C. above the temperature of the $N_2O_4$. The air containing the $NO_2$ is then passed through a receptacle or cartridge where it is converted to NO gas for delivery to the patient. Examples of such receptacles or cartridges are described, for example in U.S. Pat. No. 7,914,743, entitled "Conversion of Nitrogen Dioxide ($NO_2$) to Nitric Oxide (NO)," and U.S. Pat. No. 8,057,742, entitled "Conversion of Nitrogen Dioxide ($NO_2$) to Nitric Oxide (NO)," the disclosures of which are incorporated by reference herein.

The flow rate of the gas mixture is controlled by the small air pump (P1) and the mass of NO in the gas is controlled by the temperature of the vessel that contains the $N_2O_4$ and the diameter and length of the narrow bore restrictor. Typical diameters for the narrow bore restrictor range, for example, from 4 to 60 microns, such as 10-30 microns. It takes a finite time to heat and cool the $N_2O_4$ vessel, which depends upon the mass and heat capacity of the $N_2O_4$ vessel. A $N_2O_4$ vessel with thin metal walls would have a low heat capacity and would heat up and cool rapidly, whereas a vessel with thicker walls would take much longer to heat up and cool down. The heating is provided by resistance wire and the rate of heating is controlled by the current to the wire. Cooling is controlled by the amount of insulation that shields the vessel from the surrounding environment, and, in a well-insulated condition, the cool down time can be as long as 30 minutes. In one example a stainless steel $N_2O_4$ vessel with walls of approximately $\frac{1}{8}^{th}$ of an inch took 5-15 minutes to heat up from room temperature, depending upon the temperature change desired. A vessel with thinner walls would heat up much faster, in a time frame of 0.5 to 2 minutes. Because of heat up times of from 0.5 to 15 minutes, it is typically not possible to instantaneously change the concentration of the NO being delivered to the patient. However, in supplying NO gas to a ventilated patient, rapid changes in NO concentration are sometimes desirable, both when the NO dose is being increased and when the NO dose is being decreased. When the NO concentration is increased, energy has to be supplied to heat the vessel. When rapid heating is desired, for example to increase the concentration of delivered NO from say 5 ppm to 20 ppm, the heating rate is typically high, the temperature of the vessel will typically overshoot the target temperature and hence the system will often deliver more NO to the patient than intended. The time delay for a reduction in concentration is relatively long since the cooling of the insulated vessel takes a significant amount of time. When decreasing the NO concentration from, for example, 20 ppm to 5 ppm, the vessel will often deliver more NO than prescribed.

Figure 5:
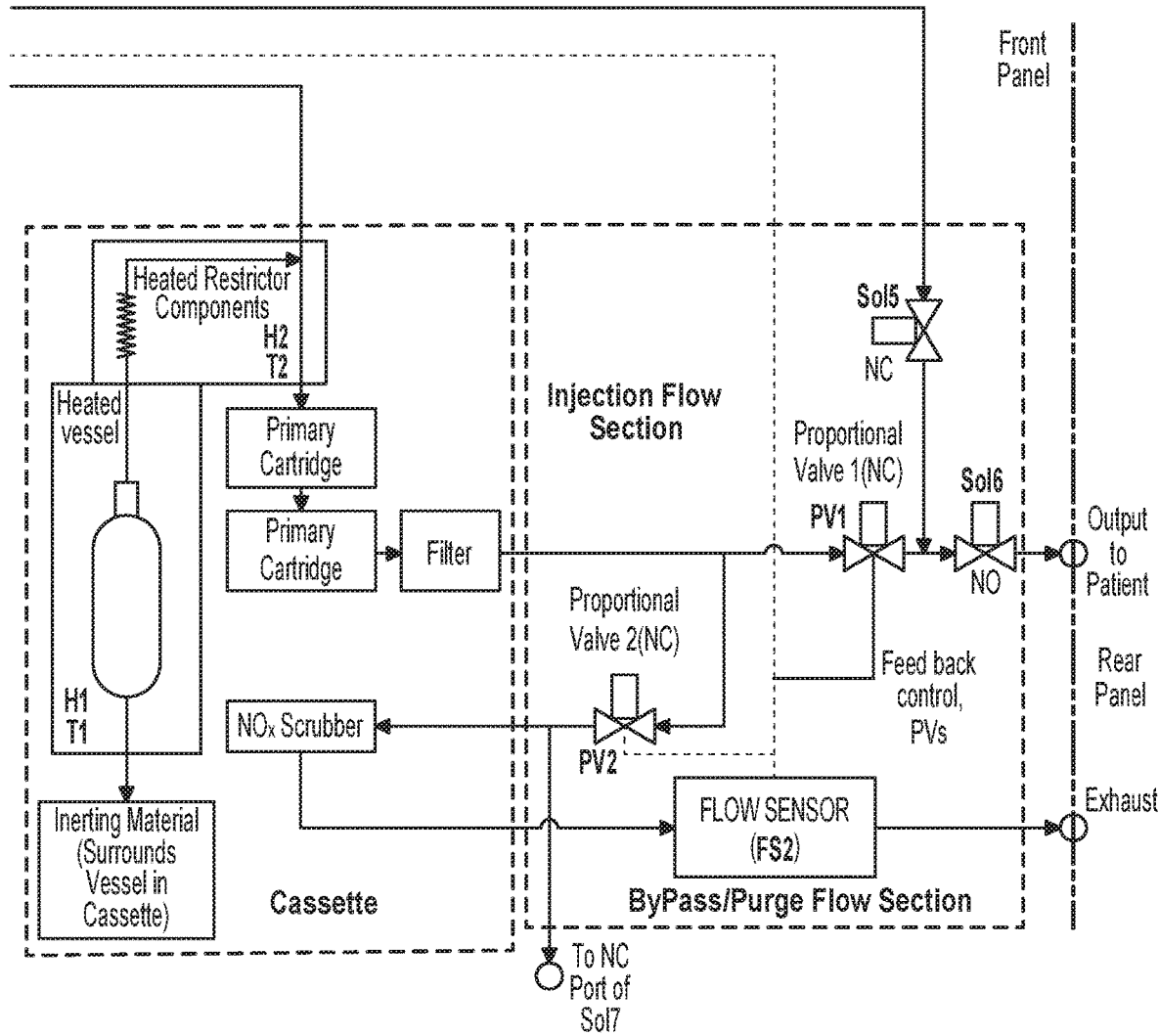
FIG. 5 is a schematic illustration showing the location of a bypass gas flow, scrubber, and a flow sensor, according to an embodiment.

FIG. 5 illustrates a system, according to an embodiment, suitable for overcoming the challenge presented by known systems of rapidly changing the concentration of NO. Dotted lines detail the boundaries of example subassemblies. It should be understood, however, that various components illustrated in one subassembly could be moved to another subassembly in another embodiment.

The embodiment depicted in FIG. 5 incorporate a bypass line and a proportional valve PV2 that takes excess NO gas sample and dumps it to a NO gas scrubber that is located in the cassette. In order to ensure that the gas that is bypassed into the room is NO and $NO_2$ free, it is exhausted through a flow sensor, FS2. The proportional valve and the flow sensor combine to provide fast but precise bypass control, typically within less than a second. Then, as the temperature stabilizes at the new set point, the bypass valve slowly closes down so that the system is once more under temperature control.

In certain embodiments, an ADS console also has a second air pump (P2) is used to deliver greater than 1 liter/min of the NO gas to the ventilator. The primary air pump typically delivers less than 1.2 L/min to the cassette, since the cassette chemistry is preconfigured for a particular flow rate (e.g., less than 1.2 L/min. In some cases, if is desired to keep the output from the ADS constant, P2 is used to provide additional flow if the scrubbed bypass is activated and it is desired to keep the injected flow into the breathing circuit constant.

In certain embodiments, the scrubber is comprised of a compound that traps NO with approximately 100% efficiency, such as a mixture of potassium permanganate and soda sorb, $Ca(OH)_2$. Other chemistries can be used as long as they scrub out the NO and $NO_2$ and prevent it from being introduced into the ambient air that is being breathed by the caregiver and the patient. The level of NO and $NO_2$ in the patient's air should not exceed the EPA environmental standards for these gases. The permanganate oxidizes the NO to produce $NO_2$ and the Sodasorb removes the $NO_2$ from the air stream. A fresh supply of the scrubber chemicals can be supplied as a built in component of the cassette, which is a consumable and typically replaced daily, or with a new patient, whichever comes first.

Calibration Cassette for Automatic Calibration Upon Loading

In certain embodiments, the calibration chemistry is built into a standard cassette and the platform is designed to be calibrated automatically whenever a new cassette is loaded. In such embodiments, calibration material can be intended for one time use, and contained in a small reservoir. In other embodiments, a special calibration cassette can be designed to plug into the front panel with the same outer interface features as a typical NO cassette, despite having a different interior. In other embodiments, the calibration cassette could also be larger than a NO cassette. In other embodiments, the calibration cassette can contain sufficient chemicals for months of calibration. Any conventional liquid chemistry can be used, including paper tape and ink jets. In certain embodiments, the platform of a calibration cassette can be wearable and a patient can calibrate from home, needing only to load a new cassette with all calibration functions being automatic.

Calibration with Gas Tanks and Computer Controlled Valves

Conventional methods of calibration involve using tanks of compressed gas that contain a precisely known concentration of either NO in nitrogen or $NO_2$ in nitrogen or air. Typically, the calibration procedure is manual and requires flowing the gas from the tank passed a sample intake into the calibration system. After the gas concentration has stabilized, the concentration as determined by the sensor is determined and compared to the concentration in the tank of standard gas. The calibration is then adjusted accordingly.

The zero gas is typically room air which has been purified to remove the gases of interest (e.g., NO and $NO_2$). The entire calibration procedure for NO and $NO_2$ can take up to 10 minutes and requires a trained operator.

Embodiments described herein facilitate tank based auto-calibration, in which conventionally manual functions are handled by a computer opening and closing various valves, with little and/or no input from the user. The tanks and all of the valves and controls are inside a single small container which can be portable. The process takes only a few minutes and requires little to no operator skill. In such embodiments, the multiple manual calibration steps and functions are simplified by providing a single container with pre-connected gas plumbing and valves operating automatically under computer control. The automation reduces likelihood of human error. There may be no requirement for gas fitting and less likelihood of leakage from connections. Typical layouts for this type of auto calibration are shown in FIG. 2 and FIG. 3.

Wearable Calibration with Docking Station

For a wearable product that is used in a home setting, calibration can be performed at a docking station that can also be operable to recharge the batteries. The calibration could be carried out while the batteries are being recharged.

- The docking station can be movable or mounted, such as on a table or wall.
- A calibration cassette can be used which attaches to the docking station. When the calibration cassette is empty, it could be replaced with a new one
- The calibration cassette can be based on the mixing of chemicals, as described above. It can also be based on using small calibration gas tanks, with automatic computer control of the valve sequence.
- The docking station could have a small Tedlar (or other suitable material) balloon inside so that a chemical and tankless calibration could be performed by diverting some of the wearable's NO output to the balloon, and measuring the rate of loss of the NO and/or the rate of increase in the $NO_2$, to carryout out the calibration. The advantage of this method for home use is that there may not be any chemicals to replace and there is no need to have a calibration cassette. This technique is described in more detail in a following section.
- The calibration cassette can be small and light enough to be portable or wearable and brought to the docking station. The docking station can be structured and programmed to receive the calibration cassette and automatically perform the calibration. On board software on the cassette or the docking station can remind the user to perform the calibration on a regular basis.
- An alternative approach would be to have the chemicals part of the active NO cassette, so that the calibration could be performed every time a new cassette was used. This calibration method may have only one calibration available for each cassette.

Fixed Parameters

Electrochemical gas sensors that are commercially available are typically highly linear in response, making a two point calibration adequate. One point is the zero calibration, the second is challenging the sensor with a known amount, typically greater than 50% of full scale response of the sensor. Performing the zero calibration is simple since it can be performed simply using room air and can be performed in the short period of time that it takes for the cassette to heat up to operational temperature and stabilize. If high precision is required for the zero calibration, the room air can be scrubbed with a scrubber such as a permanganate/Sodasorb scrubber to remove any NO or $NO_2$ that may be present in the room air. For the GeNOsyl Acute DS, there are times during weaning when very low, around 1 PPM or less, dosages are desired, which may necessitate zero-point calibration using pure (NO and/or $NO_2$ free) air. For the wearable system, scrubbing may also be necessary for delivering concentrations of less than 1 ppm (equivalent to 80 PPM at 0.2 L/min or 16 PPM at 1 L/min delivered to the nasal cannula).

The high concentration calibration can be more complex since a known source of gas is normally required. For the GeNOsyl Acute DS using a cylinder of calibration gas is practical in the hospital environment. For a wearable system having calibration gases and requiring calibration of the device can be difficult. The gas sensors can be calibrated at the factory, and any time the device is returned for service. The design of the wearable system is such that a feedback loop to control the NO concentration may not always be needed. When needed it is typically controlling the internal NO concentration at the point at which the gas exits the wearable console and is delivered to the basal cannula or mask. The cassette in the wearable system will typically be operated at a constant temperature, 45° C. for example. A simple feedback loop can be provided to control the temperature instead of the NO concentration, although directly controlling the NO concentration is the preferred method. To achieve different dosages to the patient, different cassettes can be made available, for example a low, medium and high dosage cassette, with the internal flow controlling restrictor being different for the three different cassettes. The only real unknown quantity is the conversion efficiency of the $NO_2$ to NO converting cartridge. Data exists for a fresh cartridge and how it changes efficiency as a function of time. If the NO sensor is not used as part of the feedback loop and is only used as a confirmation sensor, then it is used to (1) confirm that NO is being generated, and (2) that the NO is being generated at the desired concentration. For example, if it is expected that the output of the cassette should be 20 PPM, then typically a measured value between say 17 and 23 PPM would be acceptable, but any value between 15 to 17 or 23 to 25 PPM would generate an error message to the user to have the calibration checked, but the system would still provide therapy to the patient. For example, a value below 15 PPM or above 25 PPM would trigger an error message to the user not to use the device and to swap out the cartridge. Drift and other errors could be caused by one or more issues. Five of the most common issues resulting in drift and other errors are: (1) a problem with the cassette such as internal leaks or a blockage, (2) drift of the NO sensor, (3) drift of the flow sensor controlling the dilution flow, (4) an unusually high temperature of the NO detection sensor, and (5) non-reproducibility of the efficiency of the $N_2O_4$ to NO converting cartridge.

A computer tracking the actual concentration being measured could distinguish between random changes and gradual drift in a given direction. If the concentration drifted downward by a few percent with each cassette change, a message to calibrate could be generated before the calibration was significantly off. On the other hand, if a one-time low NO concentration were measured, and the next cassette was within calibration, then it could be assumed that the original cassette was an isolated case. Typically, the most significant drift is due to a drift of the zero. Additionally, because the zero drift is sensitive to temperature changes, the zero drift is automatically checked on loading a new cassette and automatically throughout the day at regular time intervals. The long term drift of the full scale values is relatively small and may need only be checked every 30 days while a single cassette is used. It is, however, preferred to check the full scale drift every time that a new cassette is loaded, which can typically be once per day.

According to embodiments described herein, fixed parameters can be used and programmed such that in the cassette and with known temperatures, every cassette will be substantially identical and there may be no need to conduct a span check with NO and/or $NO_2$, provided that there is a frequent zero check. Parameters that can be controlled in the cassette are the diameter and length of the restrictor tube, the position in the cassette of the restrictor tube, and the location of the heating coils, and the repeatability of the temperature control.

Real Time Calibration Without Requiring Calibration Gases

An alternative calibration technique is described here that eliminates the use of known calibration gases entirely and all of the shortcomings of requiring accurately known gas calibration standards stored in high pressure gas cylinders. Instead of relying on the accuracy and precision of the gas standard and whether or not it had degraded with time, the alternative technique is independent of the precise NO concentration. Instead, the alternative technique is based on the rate of loss of the NO concentration with time as it reacts with $O_2$ to form $NO_2$. The kinetics of the homogeneous gas-phase reaction of NO with $O_2$ to produce $NO_2$ was first studied by Bodenstein and Wachenhein in 1918, as shown in Equation 1.

$$NO + NO + O_2 \xrightarrow{k} NO_2 + NO_3 \quad \text{Equation 1}$$

Since their early research, 22 additional independent experimental studies have been carried out in 6 countries covering the temperature range of 273 to 600K, with NO partial pressures ranging from 20 parts per million (ppm) to 2,000 ppm to 200,000 ppm as shown in a recent review. As a result, the reaction of NO with $O_2$ is well documented.

The rate of formation of $NO_2$ has been shown to be first order in $O_2$, second order in NO, and third order in pressure, with the rate of formation of $NO_2$ being expressed as:

$$+d(NO_2)/dt = -d(NO)/dt = k(NO)^2(O_2) \quad \text{Equation 2}$$

According to the fundamental kinetic rate Equation 2, the rate of formation of $NO_2$, $d(NO_2)/dt$, is equal to the rate of loss of NO, $-d(NO)/dt$. The increase in the concentration of $NO_2$ and the loss of NO over a given time period can be readily determined from the change in output of the NO and $NO_2$ electrochemical sensors. The two sensors provide substantially the same slope, when normalized to unity, with the $NO_2$ slope being positive and the NO slope being negative. Furthermore, since the rate constant, k, and its temperature coefficient are well known, the NO concentration can be determined solely by measuring the rate of change of the $NO_2$ and/or the NO concentration with time, provided that the $O_2$ concentration remains constant over the course of the measurement. Prior knowledge of the precise NO concentration is therefore not required. The normalized slopes are then compared to what is expected from the kinetic rate Equation 2.

The kinetic rate Equation 2 is integrated by assuming that the oxygen is present in excess, 21% (210,000 ppm) and is therefore constant, and converting to the appropriate units, the concentration of $NO_2$ (in ppm) present at time t (in seconds) is given by:

$$(NO_2) = \frac{2.28 \times 10^{-7} t (NO)_{init}^2 (\% \ O_2)}{2.28 \times 10^{-7} t ((\% \ O_2)(NO)_{init} + 1}$$

The rate constant has been established as $k = 2.4 \times 10^9$ exp $(1046/RT)$ cm6 mol$^{-2}$ sec. A simple approximation for NO concentrations in the low ppm range gives:

$$NO_2 = 2.28 \times 10^{-7} t (NO)_{init}^2 (\% \ O_2) \quad \text{Equation 3}$$

Equation 3 can be used to calculate the theoretical $NO_2$ concentration using the known rate constant, if the NO and $O_2$ concentration are known.

Figure 6:
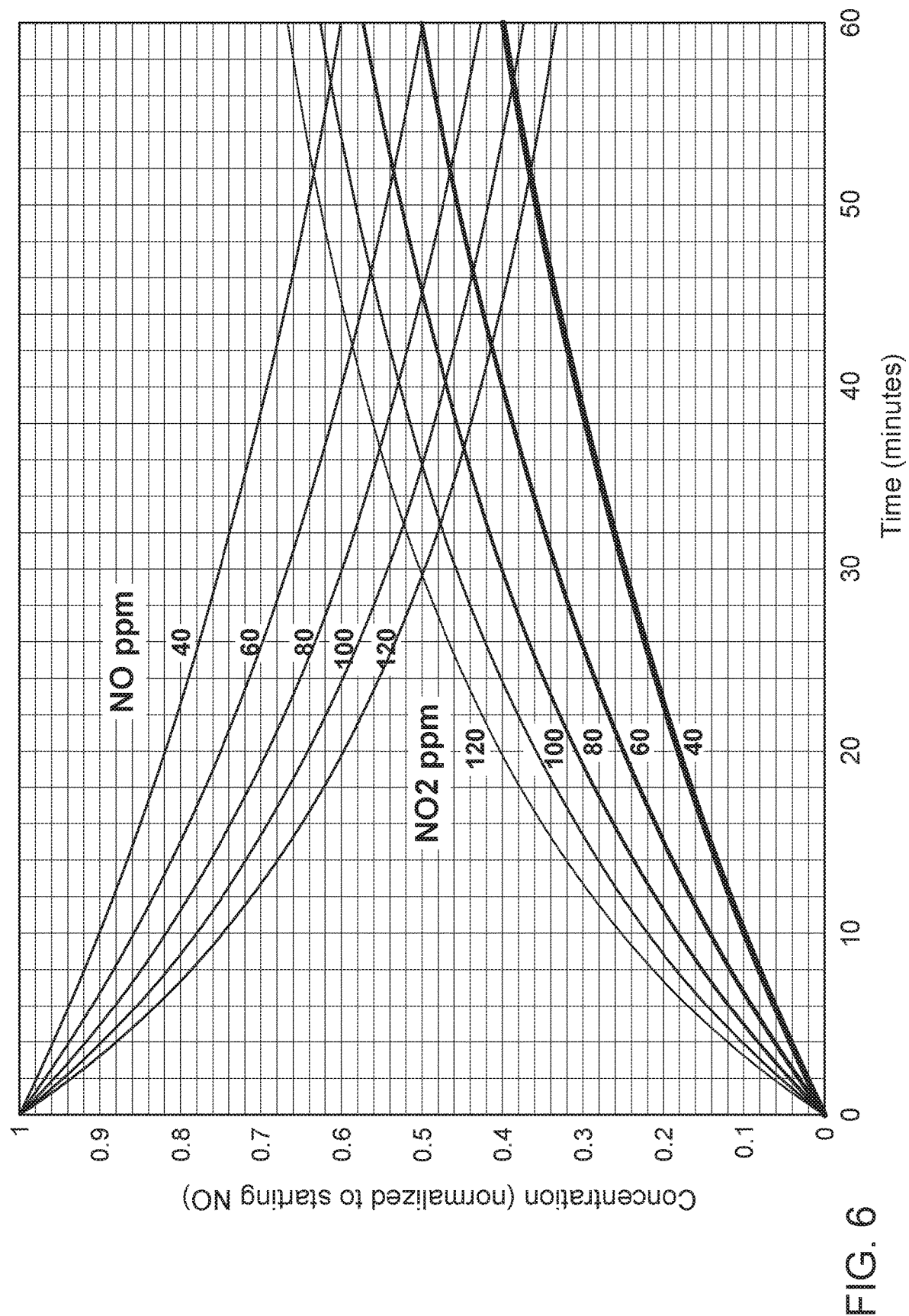
FIG. 6 shows experimental data for the conversion of NO to $NO_2$ as a function of time for up to 60 minutes, NO in ppm. O2=20%, Normalized.

Since the signal from the sensors is a function of the gain of the system, all data and ratios are normalized, thus allowing comparison without needing to correct for gain differences. Equation 3 is used to determine the change of ratio of the NO as a function of time for different NO starting concentrations. As shown in FIG. 6, there is a curvature of the plots over a time period of 60 minutes.

Figure 7:
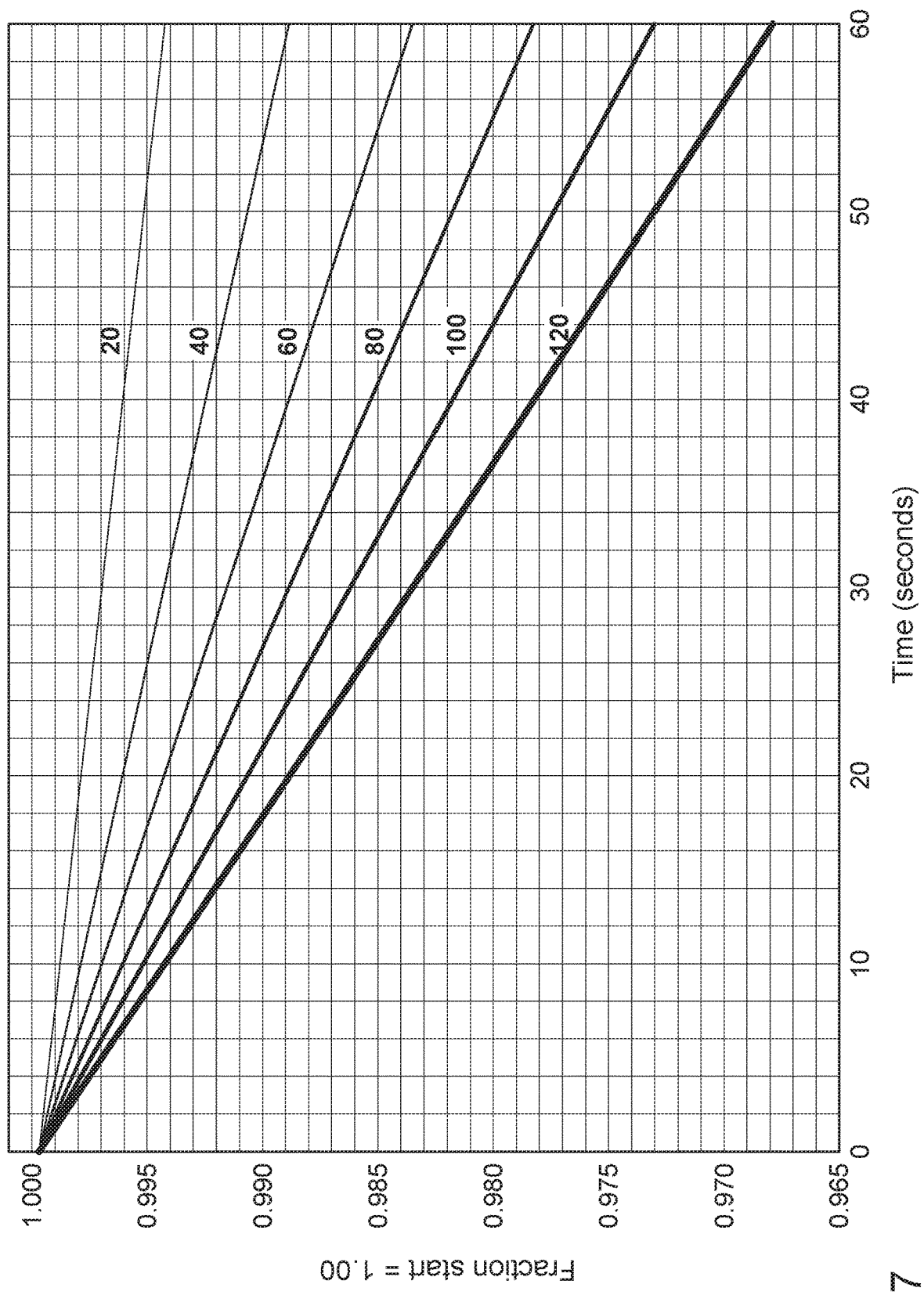
FIG. 7 shows experimental data for the NO Ratio as a function of time for up to 1 minute only, NO in ppm, O2=20%, Normalized. Note plots are a straight line over the time of interest.
Figure 8:
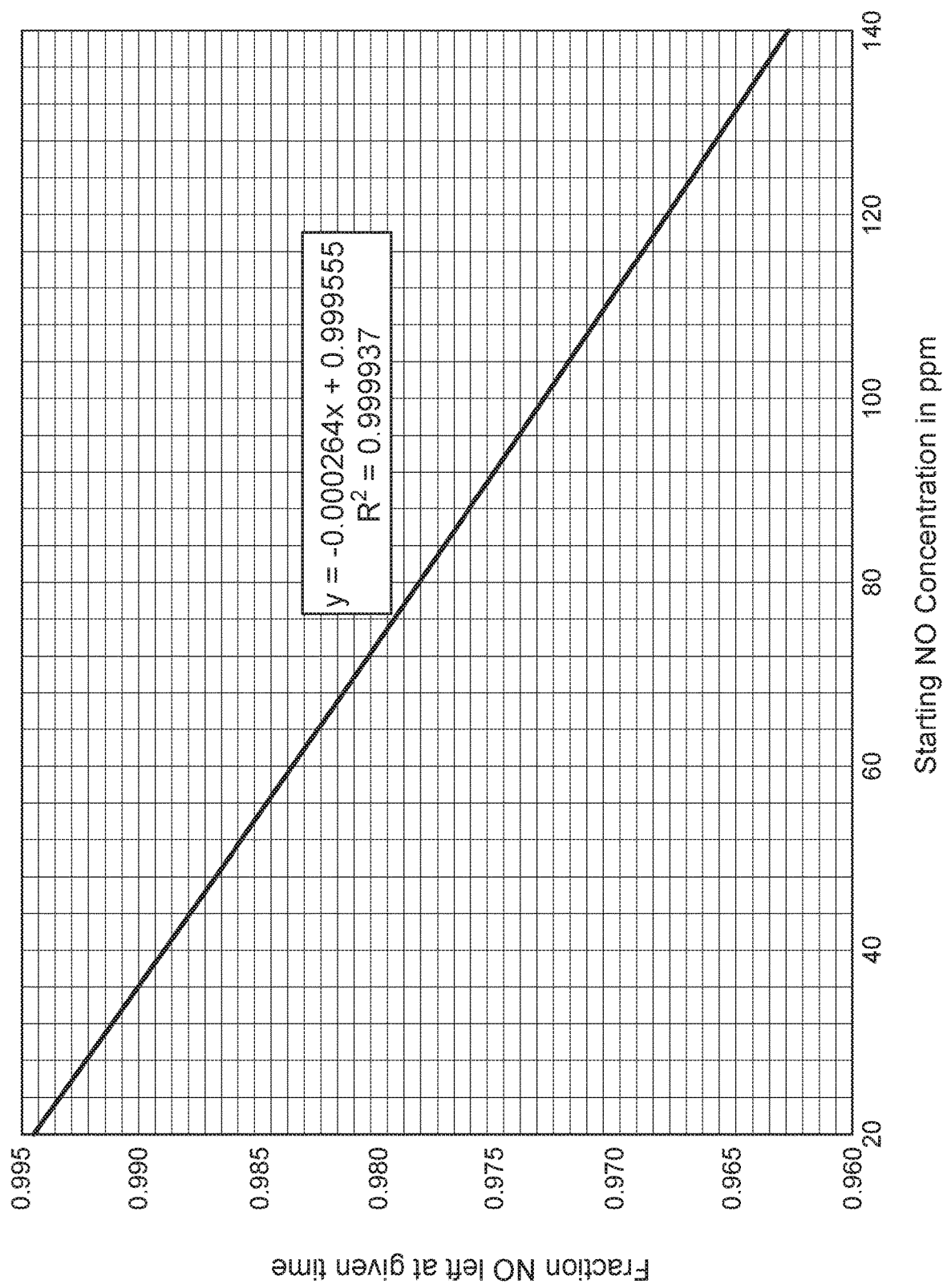
FIG. 8 shows experimental data for the fraction NO remaining at 60 seconds as a function of start time.

Over a 1 minute time period, which is a convenient time period for a practical calibration, the plots are essentially linear, as shown in FIG. 7. From the 60 second data line of FIG. 7, the expected NO ratio at different starting concentrations is shown in FIG. 8. Thus, for any ratio of NO remaining, the starting NO concentration at the beginning of the 60 second time frame is obtained. The equation of the line is also shown in FIG. 8.

Figure 9:
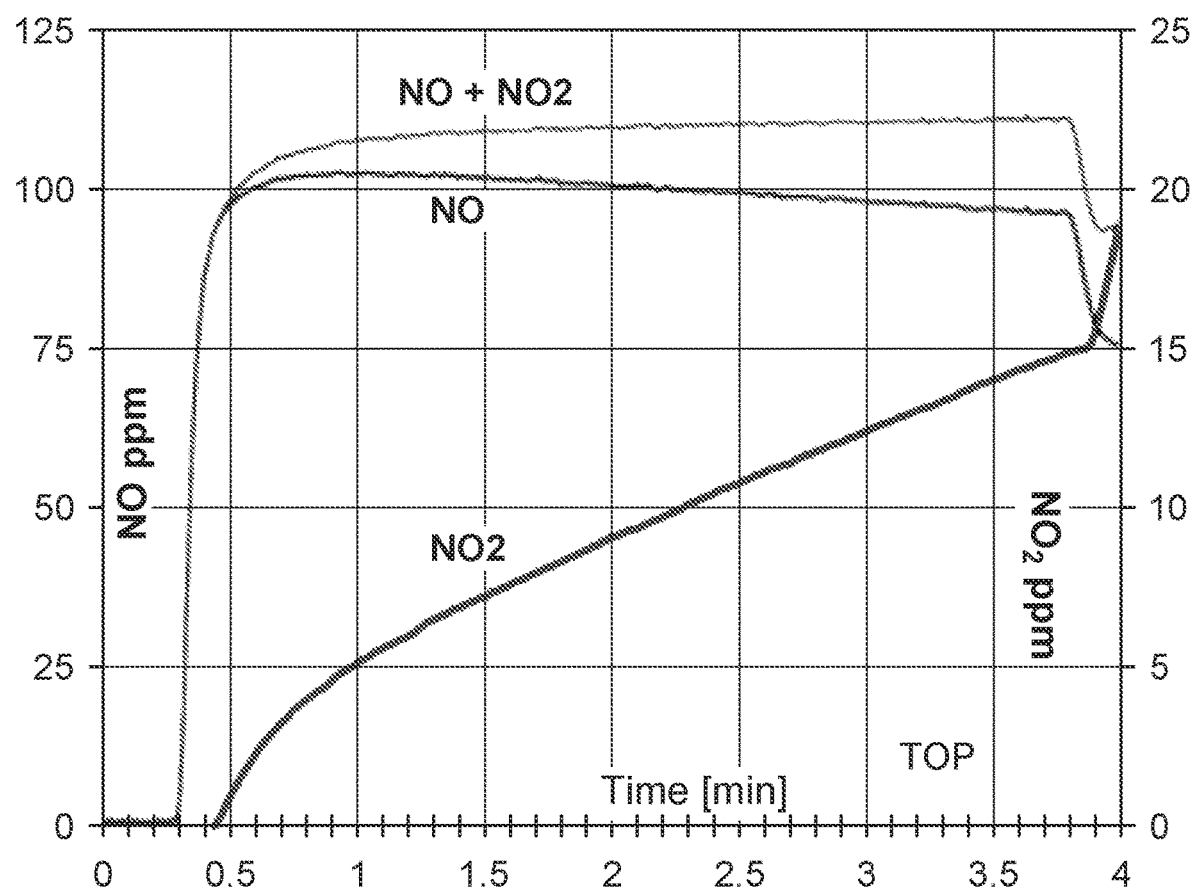
FIG. 9 shows the data plot of the output of the electrochemical sensors, showing the increase in $NO_2$, the decrease in NO and the sum of $NO_2$+NO. Note that the vertical axis for the $NO_2$ increase is 5 times greater than the NO decrease.

A practical experimental approach is to fill a small balloon with a gas containing NO in air and measure the rate of loss of NO and the rate of gain of $NO_2$ with time, and then use FIG. 8 to calculate the NO concentration of the gas. In practical terms, this is accomplished by diverting some of the NO in air that is being generated by the system, at a concentration of about 50 to 100 ppm, into, for example, a 1 liter Tedlar bag, and then withdrawing the gas from the bag as it is emptied into the sampling module. With a sampling rate of approximately 300 ml/min, this allows for about 200 seconds of continuous data. FIG. 9 is an example of the type of data that is generated, showing the decrease in the NO concentration, the increase in the $NO_2$ concentration with the sum of the NO and $NO_2$ concentrations remaining constant.

For example, at one minute an $NO_2$ formation of 1.8 ppm is formed when the NO concentration was 80 ppm. Stated another way, for example, the formation of 1.8 ppm of $NO_2$ in 60 seconds occurs if the NO concentration was 80 ppm in air. Further computation would show a doubling at 2 minutes since the formation is linearly proportional to the time. A further calibration check would be to repeat at a different NO concentration. Since the $NO_2$ is proportional to the square of the NO, this too adds a powerful confirmation to the calibration logic. The formation is also linearly proportional to the oxygen concentration. This can be varied as well as long as oxygen concentration is measured with an on board $O_2$ sensor.

At a set $O_2$ concentration, such as in air, and a set time, such as 1 minute, for example, there are a unique NO and $NO_2$ concentrations which could occur. Measurement of both NO and $NO_2$ within the calculated range, would be confirmation of the calibration. Varying the $O_2$ concentration and/or the time, would add another level of verification and provide sufficient information for a true calibration.

In certain embodiments, there are 2 NO sensors or twin NO sensors. If they gave different readings, the one that was correct would be the one that agreed with the computer calculation.

In other embodiments, calibration for the $NO_2$ sensor m performed on a regular basis, and thus the zero point can be assumed to be correct. Since the full scale calibration may be at, for example, 10 PPM while the alarm is typically set at 1 PPM, even a large full scale shift would lead to a small PPM shift at the 1 PPM region. For example, if the shift were to 8 or 12 PPM, the 1 PPM reading would be 0.8 or 1.2 PPM assuming the zero calibration is correct, not that significant since the alarm at 1 PPM was chosen to be conservative to begin with. So in one example, with NO in the system at a concentration of greater than about 50 ppm, the NO and $NO_2$ flow could be stopped. The NO and $NO_2$ concentration is measured, and as detected with the sensors, the NO is reduced and the $NO_2$ is increased by the same amount. Using the known kinetic equation for the formation of $NO_2$ from NO and oxygen to calculate both the NO and $NO_2$ and compare it to what was measured. For example, agreement within ±20% is adequate for a span check. If out of this range, the calibration can be adjusted accordingly.

In one example, the process of calibrating is conducted as follows:

While the system is operating and the sample analysis module is showing an NO signal, divert some of the flow to a balloon and then sample from the balloon for a few minutes. In a twin calibration sampling module, the second channel would continue to sample)

Record the NO signal and the $NO_2$ signal (this should read 0.0 for ADS and wearable for example).

Continue to record the NO and $NO_2$ response. The NO response should go down by the same amount that the $NO_2$ goes up. With knowledge of the $O_2$ concentration (by using air or from the $O_2$ sensor), calculate the $NO_2$ level predicted by the kinetics. NO and $NO_2$ sensors are in calibration if the $NO_2$ response corresponds to the predicted value based upon the NO response, the $O_2$ concentration and the elapsed time.

If sensors are within 20% of set value, the calibration is good.

If sensors are not within calibration, adjust to bring them into calibration Use twin NO sensors to check on NO response if there is doubt In certain embodiments, all calculations to be carried out in real time by on-board computer. The above method would provide real time on-the-fly calibration without calibration gases.

For added verification, the method can further include tracking NO and $NO_2$ response for several minutes, varying the $O_2$ response and check that $NO_2$ formation varies linearly, and varying NO response and check that $NO_2$ formation varies by the square power.

To verify that sensors are in calibration, output should show the following unique NO and $NO_2$ values in accordance with equation, NO decreases by same amount $NO_2$ increases, proportional to elapsed time, proportional to $O_2$ concentration, and square power response to NO concentration.

A calibration that does not require a precisely known value for the NO and the $NO_2$ concentration levels, reduces or eliminates the problems associated with providing low ppm level standards, which often degrade rapidly with time. It also eliminates errors associated with making up the standards. In practice, the technique of using the rate of loss of NO, or the rate of gain of $NO_2$, is a more accurate procedure and avoids the need of having to have calibration standards available, either from gas cylinders, or making them up chemically.

Spill and Scrubbed Bypass

In certain embodiments, a system can include a compartment filled with Sodasorb, which surrounds the liquid $N_2O_4$ vessel and the connections to it. It serves as an absorbent to mop up and neutralize any $N_2O_4$ or $NO_2$ that may leak out in the event of a catastrophic event. Sodasorb efficiently removes $NO_2$, which is converted into primarily calcium nitrate, and some sodium nitrate. Sodasorb® absorbent is intended for medical purposes to remove carbon dioxide from gases in the breathing circuit, and is can also be applied in systems involving anaesthesia and respiratory therapy equipment. Sodasorb® absorbents are conventionally available in two formulations for medical use: Sodasorb® for traditional flow rate systems and Sodasorb® LF for low and ultra-low flow anaesthesia systems. In diving applications Sodasorb® HP is designed for high performance removal of $CO_2$ from industrial hyperbaric diving chambers as well as military and recreational re-breather equipment. Additionally, Sodasorb® is an effective absorbent for industrial rescue equipment such as mine safety refuges and escape re-breathers.

Certain embodiments can also include a dump, which is a compartment filled with potassium permanganate and some Sodasorb. The permanganate oxidizes the NO to $NO_2$ so that it can be more readily tapped out by the Sodasorb. As an oxidant, potassium permanganate is used as an antiseptic. Certain embodiments can include both a spill and dump.

Referring to FIG. 5, the flow through the cartridges is controlled by a feedback loop between the flow sensor FS1 and proportional valve PV1. P1 is set to provide excess flow, with the excess flow automatically exhausted by use of the backpressure regulator, PR1. For the scrubbed bypass, the flow through the scrubbed bypass is controlled by PV2 along with the flow sensor FS2 that controls PV2 through a feedback loop. The flow through PV1 when the scrubbed bypass is active is still controlled by a feedback loop using FS1 along with FS2 with the algorithm calculating the actual flow as (FS1–FS2). The flow for the dilution air is controlled by a feedback loop between FS4 and P2. P2 is a single headed pump.

In certain other embodiments, P2 can be a dual headed pump. Since a physically small pump is desired to keep the ADS chassis small, and since only a single motor under feedback control is desired, under some conditions a single headed pump will not achieve the flows required, therefore, in some instances, a dual headed pump may be preferable.

Whenever the NO level is measured to be above the set point, the excess is sent to the bypass scrubber until the NO level is at the set point. In the case of reducing the NO concentration from a high to a low level, the amount of excess NO that is sent to the scrubber can be continually reduced as the temperature of the $N_2O_4$ vessel is reduced. When the temperature of the vessel has stabilized at the new set point, the amount of gas being sent to the scrubber can be reduced to zero. In the case of the need to rapidly increase the NO from a low to a high value, there may be an overshoot of the temperature so that more NO than required is generated. In this case the excess will similarly be sent to the scrubber so that the NO delivered to the patient remains exactly at the set point. The flow required through PV2, in order to obtain the desired concentration, is simply calculated from the flow ratios between PV1 and PV2 (see FIG. 5)

In other embodiments, the scrubbed bypass device and methods can be used in a system with a ventilator. In one example of such a system, there are two cassettes and two consoles. The first console is the primary or active console, and the second one being the "backup" unit. If the primary were to fail, or had enough hours of operation that the cassette charge of $N_2O_4$ was running low, the "backup" unit takes over and becomes the primary unit, with the primary unit being replaced if it failed. If the cassette was near the end of its charge, then a new cassette would be loaded into the original Primary and it would become the new backup. In other embodiments, there could be one console, and only the cassette is changed before it runs out. The cassette is designed to run out of $N_2O_4$ before the anti-oxidant cartridges are used up, and before the scrubber material is used up. In typical operation there is greater than 100% of extra antioxidant capacity, so that there is enough anti-oxidant to convert all of the $N_2O_4$ into NO. In order to have the backup unit being able to come online rapidly, the vessel containing the $N_2O_4$ that is within the cassette is heated to the operational temperature, even though the cassette has not been activated (activate here means breaking the glass ampoule that contains the $N_2O_4$). In certain embodiments, a typical operation would involve the two consoles communicating between each other electronically, and thus the backup unit could set the operational temperature identically to that of the primary unit. However, when total redundancy is required, it may be better to have two completely independent consoles that do not communicate with each other.

To enable the backup unit to achieve the desired set point quickly, the actual temperature used for the $N_2O_4$ vessel could be a few degrees higher in the backup unit than the primary unit. When the backup console is activated, the scrubber bypass would be used to quickly achieve the desired concentration set point, and then slowly drop the temperature to the proper temperature to maintain the desired set point, while also changing the flow through the scrubbed bypass until it becomes zero when the vessel is at the proper temperature to maintain the desired concentration without the scrubbed bypass. This temperature can also be optimized and determined by a controller.

Another use of the scrubbed bypass is to achieve low concentrations when required. In certain embodiments, for efficiency, the vessel can be designed to only be heated, rather than heated or cooled. Since there is not a cooler in the system to lower the temperature of the vessel, such a system is designed to operate the vessel from 35 to 70° C. To achieve very low concentration such as 1 PPM or even lower, even at 35° C., the output may be too high to achieve the desired concentration. Using the scrubbed bypass will allow the ADS to output these very low concentrations by dumping most of the output to the scrubbed bypass, thereby achieving outputs of much less than 1 PPM. Another similar condition would occur if the unit were being operated at the extreme specified temperature of 40° C. For lower concentrations, the vessel could not reach the desired temperature, even if it were 35° C. or above. Using the scrubbed bypass would allow the ADS to output the desired low concentration even in the case of extreme ambient conditions.

In certain embodiments, the scrubbed bypass is only used for short periods of time when the concentration set point is relatively high, and thus the amount of the $N_2O_4$ charge that is dumped into the atmosphere is low, and thus has a small effect on the useful lifetime of the cassette. In the case of very low concentrations the scrubbed bypass could be operational, for example, 100% of the time, however, since the concentration set point is low the amount of $N_2O_4$ dumped is also low, and thus the cassette can still meet the specified life time.

In certain embodiments, the bypass scrubber can also be used if the ADS is put into standby mode. The system is designed to insure that once a cassette is used it cannot be removed and re-used again. Thus, if a used cassette is removed from the ADS there is a lockout mechanism that insures that the cassette cannot be used again. Also, if the power to the ADS were turned off and the cassette was left in the ADS, the cassette already inside the ADS will look like a used cassette, and the ADS will not operate with that cassette. Thus, in order to allow use of a cassette under certain conditions "multiple" times, there is a standby condition. In the standby condition, the cassette is not deactivated, nor is the ADS powered down. In the standby position the temperature of the vessel containing the $N_2O_4$ is reduced to ambient so as to minimize the $N_2O_4$ usage, and all of the output of the cassette is passed into the scrubbing material in the cassette. At ambient conditions of less than approximately 30° C., there will not be enough pressure in the vessel to force the $NO_2$ through the restrictor tube, and the flow will be very low and controlled not by classical fluid dynamics but by gas diffusion. When it is desired to use the ADS again with the current cassette, the scrubbed bypass is turned off, or used in the normal dilution mode, the vessel heated to the desired temperature and therapy to the patient can occur.

The generated NO can be delivered to a mammal, which can be a human. To facilitate delivery of the NO, a system can include a patient interface. Examples of a patient interface can include a mouth piece, nasal cannula, face mask, fully-sealed face mask or an endotracheal tube. A patient interface can be coupled to a delivery conduit. A delivery conduit can include a ventilator or an anaesthesia machine. In some cases the gas can be delivered via a cannula to a wound, to an internal organ such as the stomach, colon, ear, or anywhere in or on the body that NO may have a therapeutic effect or purpose. Since NO is known to prevent the replication of rapidly growing cells, it could also be used to deliver NO to the site of a bacterial or viral infection, or to a malignant cancer.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed:

1. A method, comprising:
   releasing droplets of a nitrite-containing solution to a target;
   releasing droplets of an acidic solution to the target;
   measuring, with a gas sensor, a concentration of nitric oxide (NO) gas produced by a mixture of the droplets of the nitrite-containing solution and the droplets of the acidic solution; and
   adjusting a calibration parameter of the gas sensor based on the concentration of NO gas.

2. The method of claim 1, further comprising controlling at least one of a rate at which droplets of the nitrite-containing solution or the droplets of the acidic solution are released to the target to produce a known concentration of NO.

3. The method of claim 1, wherein at least one of the droplets of the nitrite-containing solution or the droplets of the acidic solution are released via at least one proportional valve.

4. The method of claim 1, wherein at least one of the droplets of the nitrite-containing solution or the droplets of the acidic solution are released via at least one ink-jet style proportional valve.

5. The method of claim 1, wherein the target is absorbent.

6. The method of claim 1, further comprising:
inserting a cassette into a console that includes the gas sensor and is configured to automatically adjust the calibration parameter upon insertion of the cassette,
the cassette including the nitrite-containing solution, the acidic solution, a reservoir containing dinitrogen tetroxide ($N_2O_4$) and configured to release nitrogen dioxide ($NO_2$), and a cartridge configured to reduce nitrogen dioxide ($NO_2$) to produce NO for inhalation.

7. The method of claim 1, wherein the concentration of NO is measured over a period of time, the method further comprising:
integrating the concentration of NO over the period of time,
the calibration parameter adjusted based on a comparison of the concentration of NO integrated over the period of time to an expected value.

8. The method of claim 1, wherein a quantity and a concentration of nitrite in the droplets of the nitrite-containing solution are known such that when the droplets of the nitrite-containing solution and the droplets of the acidic solution mix at the target a known quantity of NO is produced.

9. The method of claim 1, wherein:
a quantity and a concentration of nitrite in the droplets of the nitrite-containing solution are known such that when the droplets of the nitrite-containing solution and the droplets of the acidic solution mix at the target a known quantity of NO is produced; and
a quantity and a concentration of acid in the droplets of the acidic solution are sufficient to completely react the quantity of the nitrite.

10. The method of claim 1, further comprising waiting a predetermined time after releasing the droplets of the nitrite-containing solution and releasing the droplets of the acidic solution before measuring the concentration of NO.

11. The method of claim 10, wherein the predetermined time is shorter than it takes for a reaction of nitrite in the nitrite-containing solution and acid in the acidic solution to reach pseudoequilibrium.

12. The method of claim 1, further comprising:
waiting a predetermined time after releasing the droplets of the nitrite-containing solution and releasing the droplets of the acidic solution before; and
sweeping gasses generated by a reaction between the nitrite and the acid across the sensor to measure the concentration of NO after waiting the predetermined time.

13. The method of claim 1, wherein the concentration of NO is measured over a period of time, the method further comprising:
integrating the concentration of NO over the period of time.

14. The method of claim 1, wherein the concentration of NO is measured over a period of time, the method further comprising:
integrating the concentration of NO over the period of time,
the calibration parameter adjusted based on a comparison of the concentration of NO integrated over the period of time to an expected value.

\* \* \* \* \*

UNITED STATES PATENT AND TRADEMARK OFFICE
CERTIFICATE OF CORRECTION

| | | |
|---|---|---|
| PATENT NO. | : 11,754,538 B1 | |
| APPLICATION NO. | : 16/511928 | |
| DATED | : September 12, 2023 | |
| INVENTOR(S) | : David H. Fine et al. | |

It is certified that error appears in the above-identified patent and that said Letters Patent is hereby corrected as shown below:

In the Specification

Column 1, Line 8 reading:
Pat. App. Ser. No. 62/699,771, entitled "Method and Appa-
Should read:
Pat. App. Ser. No. 62/699,772, entitled "Method and Appa- Signed and Sealed this
Thirty-first Day of October, 2023

Katherine Kelly Vidal
*Director of the United States Patent and Trademark Office*